(12) United States Patent
Buchanan et al.

(10) Patent No.: US 6,573,396 B2
(45) Date of Patent: Jun. 3, 2003

(54) CO-PRODUCTION OF DIALKYL CARBONATES AND DIOLS WITH TREATMENT OF HYDROXY ALKYL CARBONATE

(75) Inventors: J. Scott Buchanan, Lambertville, NJ (US); Jose G. Santiesteban, Bethlehem, PA (US); Zhaozhong Jiang, Edison, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 09/976,608

(22) Filed: Oct. 12, 2001

(65) Prior Publication Data

US 2003/0078448 A1 Apr. 24, 2003

(51) Int. Cl.$^7$ .......................... C07C 69/96; C07C 29/00
(52) U.S. Cl. ........................................ 558/277; 568/840
(58) Field of Search ........................... 558/277; 568/840

(56) References Cited

U.S. PATENT DOCUMENTS

| | | |
|---|---|---|
| 3,642,858 A | 2/1972 | Fevel et al. |
| 4,181,676 A | 1/1980 | Buysch et al. |
| 4,218,391 A | 8/1980 | Romano et al. |
| 4,226,778 A | 10/1980 | Venturello et al. |
| 4,231,937 A | 11/1980 | Kao et al. |
| 4,233,221 A | 11/1980 | Raines et al. |
| 4,325,874 A | 4/1982 | Jacobson |
| 4,434,105 A | 2/1984 | Buysch et al. |
| 4,661,609 A | 4/1987 | Knifton |
| 4,691,041 A | 9/1987 | Duranleau et al. .......... 558/277 |
| 5,430,170 A | 7/1995 | Urano et al. |
| 5,436,362 A | 7/1995 | Kondoh et al. |
| 5,498,743 A | 3/1996 | Shih et al. |
| 5,847,189 A | 12/1998 | Tojo et al. |
| 6,162,940 A | 12/2000 | Chang et al. ................ 558/277 |
| 6,166,240 A | * 12/2000 | Chang et al. ................ 558/277 |

FOREIGN PATENT DOCUMENTS

| | | |
|---|---|---|
| EP | 478073 A2 | 1/1992 |
| EP | 0 638 541 A1 | 2/1995 |
| JP | 54003012 | 1/1979 |
| JP | 3-44354 | 2/1991 |
| JP | 6-107601 | 4/1994 |

OTHER PUBLICATIONS

Cella, James A., et al., *Preparation of Dialkyl Carbonates via the Phase–Transfer–Catalyzed Alkylation of Alkali Metal Carbonate and Bicarbonate Salts*, J. Org. Chem., 49, pp. 1122–1125 (1984).

Fujinami, Tatsuo, et al., *A Facile Preparation of Dialkyl Carbonates from Potassium Carbonate and Alkyl Bromides by Using Organostannyl Compound as a Catalyst*, Chemistry Letters, pp. 749–752 (1981).

Romano, Ugo, et al., *Synthesis of Dimethyl Carbonate from Methanol, Carbon Monoxide, and Oxygen Catalyzed by Copper Compounds*, Ind. Eng. Chem. Prod. Res. Dev., 19, pp. 396–403 (1980).

Tundo, Pietro, et al., *Continuous–Flow Processes under Gas–Liquid Phase–Transfer Catalysis (GL–PTC) Conditions: The Reaction of Dialkyl Carbonates with Phenols, Alcohols, and Mercaptans*, Ind. Eng. Chem. Res., 27, pp. 1565–1571 (1988).

Chin, Yu–Ren, et al., *Dimethyl Carbonate from Methanol by Non–Phosgenation Processes*, Process Economics Program, PEP Review No. 87–1–4, (Jul. 1988).

DATABASE WPI; Section Ch, Week 200234 Derwent Publications Ltd., London, GB; Class A41, AN 2002–297151 XP002216409 & JP 2001 316332 A (Nippon Shokubai Co Ltd), Nov. 13, 2001 (Nov. 13, 2001) Abstract.

Knifton, John F., et al., *Ethylene Glycol–Dimethyl Carbonate Cogeneration*, Journal of Molecular Catalysis, 67 (1991) pp. 389–399.

\* cited by examiner

Primary Examiner—T A Solola
Assistant Examiner—Joseph Murray

(57) ABSTRACT

A process for the production of a dialkyl carbonate and a diol from a cyclic carbonate and an aliphatic monohydric alcohol wherein the cyclic carbonate and aliphatic monohydric alcohol are reacted in the presence of a transesterification catalyst to form a crude product stream which contains a dialkyl carbonate, a diol, a hydroxy alkyl carbonate, which is formed as an intermediate of the two step transesterification reaction, unreacted aliphatic monohydric alcohol and unreacted cyclic carbonate. The dialkyl carbonate and unreacted aliphatic monohydric alcohol are separated from the crude product stream and then the hydroxy alkyl carbonate is diminished, reduced or eliminated from the crude product stream, prior to the separation and purification steps needed to recover the diol, resulting in improved yields and product purity.

44 Claims, 3 Drawing Sheets

US 6,573,396 B2

CO-PRODUCTION OF DIALKYL CARBONATES AND DIOLS WITH TREATMENT OF HYDROXY ALKYL CARBONATE

This invention relates to a process for preparing dialkyl carbonates and diols. More specifically the present invention relates to a process for preparing dialkyl carbonates and diols from cyclic carbonates and alcohols with substantially diminished levels of hydroxy alkyl carbonate by-product.

BACKGROUND OF THE INVENTION

Dialkyl carbonates are important intermediates for the synthesis of fine chemicals, pharmaceuticals and plastics and are useful as synthetic lubricants, solvents, plasticizers and monomers for organic glass and various polymers, including polycarbonate, a polymer known for its wide range of uses based upon its characteristics of transparency, shock resistance and processability.

One method for the production of polycarbonate resin employs phosgene and bisphenol-A as starting materials. However, this method has numerous drawbacks, including the production of corrosive by-products and safety concerns attributable to the use of the highly toxic phosgene. As such, polycarbonate manufacturers have developed non-phosgene methods for polycarbonate production, which use diphenyl carbonate and bisphenol-A as starting materials. Diphenyl carbonate can be prepared from phenol and dimethyl carbonate.

Dimethyl carbonate has a low toxicity and can also be used to replace toxic intermediates, such as phosgene and dimethyl sulphate, in many reactions, such as the preparation of urethanes and isocyanates, the quaternization of amines and the methylation of phenol or naphthols. Moreover, it is not corrosive and it will not produce environmentally damaging by-products. Dimethyl carbonate is also a valuable commercial product finding utility as an organic solvent, an additive for fuels, and in the production of other alkyl and aryl carbonates.

Dimethyl carbonate, as well as other dialkyl carbonates, have traditionally been produced by reacting alcohols with phosgene. These methods have the same problems as methods that use phosgene and bisphenol-A, i.e., the problems of handling phosgene and disposing of phosgene waste materials. Thus, there is a need for commercially viable non-phosgene methods for the production of dimethyl carbonate, as well as other dialkyl carbonates. Non-phosgene methods that have been proposed for producing dialkyl carbonates include the transesterification reaction of alcohols and cyclic carbonates. Most of the proposed methods relate to the use of various catalysts for that reaction. Examples of such proposed catalysts include alkali metals or basic compounds containing alkali metals; tertiary aliphatic amines; thallium compounds; tin alkoxides; alkoxides of zinc, aluminum and titanium; a mixture of a Lewis acid and a nitrogen-containing organic base; phosphine compounds; quaternary phosphonium salts; cyclic amidines; compounds of zirconium, titanium and tin; a quaternary ammonium group-containing strongly basic anion-exchange solid material; a solid catalyst selected from the group consisting of a tertiary amine or quaternary ammonium group-containing ion-exchange resin, a strongly acidic or a weakly acidic ion-exchange resin, a mixture of an alkali metal with silica, a silicate of an alkaline earth metal and an ammonium ion-exchanged zeolite; and a homogeneous catalyst selected from the group consisting of tertiary phosphine, tertiary arsine, tertiary stibine, a divalent sulfur compound and a selenium compound.

The catalytic transesterification of a cyclic carbonate with an alcohol involves two equilibrium steps which can generate a hydroxy alkyl carbonate as the reaction intermediate. For example, in the transesterification of ethylene carbonate (EC) with methanol (MeOH), the intermediate which is formed is 2-hydroxyethyl methyl carbonate (HEMC). This two equilibrium step reaction may be represented by the following:

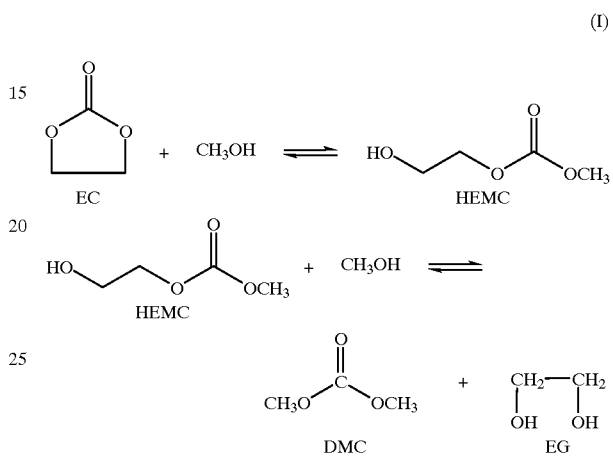

The amount of hydroxy alkyl carbonate, e.g., HEMC in the case of EC and MeOH, formed is dependent on the type of catalyst employed and reaction conditions used in the process. There can be a significant amount of unreacted hydroxy alkyl carbonate (e.g., HEMC) following the second equilibrium step. Glycols present in the reaction mixture may also react with a cyclic alkyl carbonate to form dihydroxy alkyl carbonates, which may be included as a type of hydroxy alkyl carbonate, and can be decomposed by means discussed herein.

Hydroxy alkyl carbonates are generally highly reactive and thermally unstable organic compounds. Thus, any attempt to separate such compounds from the desired products using typical separation techniques, such as high temperature distillation, would likely cause at least partial decomposition and/or reaction with other organics in the product stream to form by-products and lower reaction yields. In the case of the transesterification of EC with MeOH, possible side reactions include inter- and intra-molecular dehydration of HEMC and dehydration between HEMC and EG.

In addition to lower yields of desired products, the side reactions will likely result in lower purity products or additional capital and operating costs needed to improve product purity.

Thus, there is a need for a process for the production of dialkyl carbonates and diols from cyclic carbonates and alcohols which does not have the above mentioned disadvantages.

SUMMARY OF THE INVENTION

According to the present invention, it has now been found that a dialkyl carbonate and diol, and more specifically dimethyl carbonate and ethylene glycol, can be prepared with high yields and high product purity, from a cyclic carbonate and an aliphatic monohydric alcohol.

The process of the present invention involves:
(a) reacting a cyclic carbonate with an aliphatic monohydric alcohol in the presence of a transesterification catalyst in a transesterification reaction zone to provide a crude product stream containing a dialkyl carbonate, diol, hydroxy alkyl carbonate, unreacted cyclic carbonate and unreacted aliphatic monohydric alcohol;
(b) separating a crude dialkyl carbonate product stream containing dialkyl carbonate and unreacted aliphatic monohydric alcohol from the crude product stream;
(c) diminishing, reducing or eliminating the hydroxy alkyl carbonate from the crude product stream; and
(d) recovering the dialkyl carbonate and the diol.

Preferably, the cyclic carbonate of the present invention is of the formula:

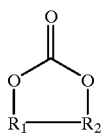

(II)

wherein $R_1$ and $R_2$ independently of one another denote a group represented by the formula $-(CH_2)_m-$, wherein m is an integer from about 1 to about 3, which is unsubstituted or substituted with at least one substituent selected from the group consisting of a $C_1$–$C_{10}$ alkyl group and a $C_6$–$C_{10}$ aryl group, wherein $R_1$ and $R_2$ can share the same substituent; and the aliphatic monohydric alcohol is of the formula:

$R_3$—OH     (III)

wherein $R_3$, is an aliphatic $C_1$–$C_{12}$ hydrocarbon group which is unsubstituted or substituted with at least one substituent selected from the group consisting of a $C_1$–$C_{10}$ alkyl group or a $C_6$–$C_{10}$ aryl group.

In one embodiment, the hydroxy alkyl carbonate is diminished from the crude product stream by:
(i) directing the crude product stream to a conversion reaction zone; and
(ii) converting at least a portion of the hydroxy alkyl carbonate in the conversion reaction zone under conversion conditions to provide additional cyclic carbonate and additional aliphatic monohydric alcohol.

Preferably, substantially all of the hydroxy alkyl carbonate is converted in the conversion reaction zone to additional cyclic carbonate and additional aliphatic monohydric alcohol.

In a preferred embodiment, substantially all of the unreacted aliphatic monohydric alcohol will be removed from the crude product stream, as a result of separating the crude dialkyl carbonate stream.

Preferably, the unreacted aliphatic monohydric alcohol separated from the crude product stream is recycled to the transesterification reactor by:
(i) separating the unreacted aliphatic monohydric alcohol from the crude dialkyl carbonate product stream; and
(ii) recycling the unreacted aliphatic monohydric alcohol to the transesterification reaction.

In yet another embodiment, after separating the crude dialkyl carbonate product stream from the crude product stream and converting the hydroxy alkyl carbonate to additional cyclic carbonate and aliphatic monohydric alcohol, the conversion products will be recycled by:

(i) separating the additional aliphatic monohydric alcohol from the crude product stream;
(ii) recycling the additional aliphatic monohydric alcohol to the transesterification reaction;
(iii) separating the additional cyclic carbonate from the crude product stream; and
(iv) recycling the additional cyclic carbonate to the transesterification reaction.

In a preferred embodiment, the cyclic carbonate is ethylene carbonate, the aliphatic monohydric alcohol is methanol, the dialkyl carbonate is dimethyl carbonate, the diol is ethylene glycol and the hydroxy alkyl carbonate is 2-hydroxyethyl methyl carbonate.

In still another embodiment according to the present invention, a process for the production of a dialkyl carbonate and a diol from a cyclic carbonate and an aliphatic monohydric alcohol comprises: (a) reacting a cyclic carbonate with an aliphatic monohydric alcohol in the presence of a transesterification catalyst to provide a crude product stream comprising a dialkyl carbonate, diol, hydroxy alkyl carbonate, unreacted cyclic carbonate and unreacted aliphatic monohydric alcohol; (b) treating the crude product stream under reaction conditions sufficient to at least partially decompose the hydroxy alkyl carbonate, thereby forming a crude dialkyl carbonate product stream; and (c) recovering the dialkyl carbonate and the diol from the crude dialkyl carbonate product stream.

Another process according to the present invention which is capable of producing a dialkyl carbonate and a diol from a cyclic carbonate and an aliphatic monohydric alcohol comprising: (a) reacting a cyclic carbonate with an aliphatic monohydric alcohol in the presence of a transesterification catalyst to provide a crude product stream comprising a dialkyl carbonate, diol, hydroxy alkyl carbonate, unreacted cyclic carbonate and unreacted aliphatic monohydric alcohol; (b) separating the dialkyl carbonate and the unreacted aliphatic monohydric alcohol from the crude product stream, thereby forming a crude dialkyl carbonate product stream and a hydroxy alkyl carbonate-rich stream; (c) treating the hydroxyl alkyl carbonate-rich stream under reaction conditions sufficient to at least partially decompose the hydroxy alkyl carbonate, thereby forming a diol-rich stream, a cyclic carbonate rich-stream and a aliphatic monohydric alcohol-rich stream; and (d) recovering the dialkyl carbonate from the crude dialkyl carbonate product stream and the diol from the diol-rich stream.

Yet another process for the production of a dialkyl carbonate and a diol from a cyclic carbonate and an aliphatic monohydric alcohol comprising: (a) in a reactive distillation vessel, reacting a cyclic carbonate with an aliphatic monohydric alcohol in the presence of a transesterification catalyst to provide a crude dialkylcarbonate product stream comprising dialkyl carbonate and unreacted aliphatic monohydric alcohol, and a hydroxyl alkyl carbonate-rich stream; (b) treating the hydroxyl alkyl carbonate-rich stream under reaction conditions sufficient to at least partially decompose the hydroxy alkyl carbonate, thereby forming a diol-rich stream, a cyclic carbonate rich-stream and a aliphatic monohydric alcohol-rich stream; and (c) recovering the dialkyl carbonate and the diol from the crude dialkyl carbonate product stream.

The present invention provides the advantage of diminishing the hydroxy alkyl carbonate from the product stream under mild conditions and producing dialkyl carbonates and diols in relatively high yield and purity from cyclic carbonates and alcohols.

While the present invention has been described and illustrated by reference to particular embodiments, those of ordinary skill in the art will appreciate that the invention lends itself to variations not necessarily illustrated herein. For this reason then reference should be made solely to the appended claims for purposes of determining the true scope of the present invention.

DETAILED DESCRIPTION OF THE PREFERRED EMBODIMENTS

Figure 1:
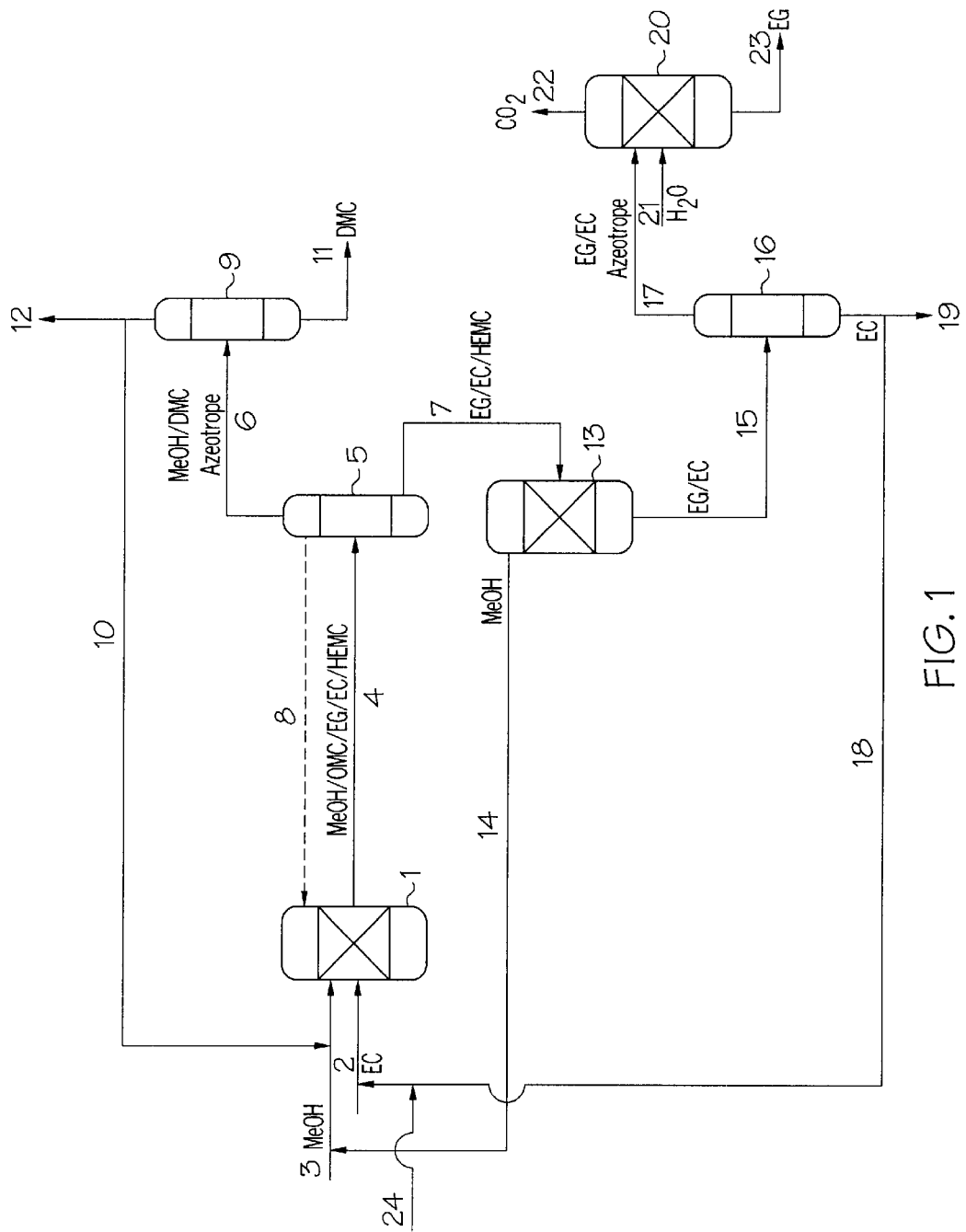
FIG. 1 is a schematic representation of a process according to the present invention which utilizes a heterogeneous transesterification catalyst.

The present invention is a process for preparing dialkyl carbonates and diols from cyclic carbonates and aliphatic monohydric alcohols, wherein the hydroxy alkyl carbonate by-product is substantially reduced or eliminated.

In preparing the dialkyl carbonates and diols, a cyclic carbonate is reacted with an aliphatic monohydric alcohol in the presence of a transesterification catalyst. Preferably, the cyclic carbonate is represented by structural formula (II) above. Examples of such cyclic carbonates include, but are not limited to, ethylene carbonate, propylene carbonate, 4-ethyl-1, 3-dioxolan-2-one; 4, 5-dimethyl-1, 3-dioxolan-2-one; 4-phenyl-1, 3-dioxolan-2-one, and the like. Of these cyclic carbonates, ethylene carbonate and propylene carbonate are preferably used because of their ready availability and high demand for their resultant carbonates. Ethylene carbonate is most preferably used.

Preferably, the aliphatic monohydric alcohol is represented by structural formula (III) above and has a boiling point lower than that of the produced diol. The type of aliphatic monohydric alcohol which can be used in the present invention varies depending on the particular cyclic carbonate produced by the carbonation reaction. Examples of such aliphatic monohydric alcohols include, but are not limited to, methanol, ethanol, n-propanol, iso-propanol, alkyl alcohol, butanol (including isomers of butanol), 3-butene-1-ol, amyl alcohol (isomers), hexyl alcohol (isomers), heptyl alcohol (isomers), octyl alcohol (isomers), nonyl alcohol (isomers), decyl alcohol (isomers), undecyl alcohol (isomers), dodecyl alcohol (isomers), cyclopentanol, cyclohexanol, cycloheptanol, cyclooctanol, methylcyclopentanol (isomers), ethylcyclopentanol (isomers), methylcyclohexanol (isomers), ethylcyclohexanol (isomers), dimethylcyclohexanol (isomers), diethylcyclohexanol (isomers), phenylcyclohexanol (isomers), benzyl alcohol, phenethyl alcohol (isomers), phenylpropanol (isomers), and the like. The above mentioned aliphatic monohydric alcohol may be substituted with at least one substituent, such as a halogen atom, a lower alkoxy group, a cyano group, an alkoxycarbonyl group, an aryloxycarbonyl group, an acyloxy group, a nitro group or the like.

Of these aliphatic monohydric alcohols, an alcohol having 1 to 6 carbon atoms is preferably used. When ethylene carbonate is the cyclic carbonate, an alcohol having 1 to 4 carbon atoms, i.e., methanol, ethanol, propanol (isomers) or butanol (isomers), is preferably used. The method of the present invention can be employed advantageously especially when methanol and ethylene carbonate are used as feedstocks for the transesterification reaction.

The transesterification reaction between the cyclic carbonate and the aliphatic monohydric alcohol involves two equilibrium steps which include the formation of a hydroxy alkyl carbonate as the reaction intermediate. The two equilibrium step reactions may be represented by the following:

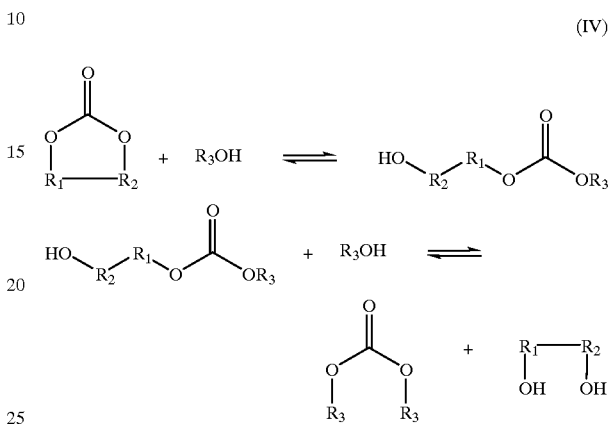

(IV)

wherein $R_1$ and $R_2$ independently of one another denote a group represented by the formula —$(CH_2)_m$—, wherein m is an integer from 1 to 3, which is unsubstituted or substituted with an least one substituent selected from the group consisting of a $C_1$–$C_{10}$ alkyl group and a $C_6$–$C_{10}$ aryl group, wherein $R_1$ and $R_2$ can share the same substituent; and $R_3$ is an aliphatic $C_1$–$C_{12}$ hydrocarbon group which is unsubstituted or substituted with at least one substituent selected from the group consisting of a $C_1$–$C_{10}$ alkyl group and a $C_6$–$C_{10}$ aryl group.

The reactants to the transesterification reaction (i.e., the cyclic carbonate and the aliphatic monohydric alcohol) are contacted in the presence of a transesterification catalyst. The transesterification catalyst can typically include any homogeneous and/or heterogeneous catalyst known in the art which provides adequate reaction kinetics and minimizes side reactions with the impurities contained in the cyclic carbonate.

Examples of such catalysts include, but are not limited to, alkali metals or alkaline earth metals, such as lithium, sodium, potassium, rubidium, cesium, magnesium, calcium, strontium, barium and the like; basic compounds such as hydrides, hydroxides, alkoxides, aryloxides and amides of alkali metals or alkaline earth metals and the like; basic compounds, such as carbonates and hydrogencarbonates of alkali metals or alkaline earth metal, alkali metal or alkaline earth metal salts of organic acids and the like; tertiary amines such as triethylamine, tributylamnine, trihexylamine, benzyldiethylamine and the like; nitrogen-containing heteroaromatic compounds, such as N-alkylpyrrole, N-alkylindole, oxazole, N-alkylimidazole, N-alkylpyrazole, oxadiazole, pyridine, alkylpyridine, quinoline, alkylquinoline, isoquinoline, alkylisoquinoline, acridine, alkylacridine, phenanthroline, alkylphenanthroline, pyrimidine, alkylpyrimidine, pyradine, alkylpyradine, triazine, alkyltriazine and the like; cyclic amidines, such as diazabicycloundecene (DBU), diazabicyclononene (DBN) and the like; thallium compounds, such as thallium oxide, thallium halides, thallium hydroxide, thallium carbonate, thallium nitrate, thallium sulfate, thallium salts of organic acids and the like; tin compounds, such as tributylmethoxytin, tributylethoxytin, dibutyldimethoxytin, diethyldiethoxytin, dibutyldiethoxytin, dibutylphenoxytin, diphenylmethoxytin, dibutyltin acetate, tributyltin chloride, tin 2-ethylhexanoate and the like; zinc compounds, such as dimethoxyzinc, diethoxyzinc, ethylenedioxyzinc, dibutoxyzinc and the like; aluminum compounds such as aluminum trimethoxide, aluminum triisopropoxide, aluminum tributoxide and the like; titanium compounds, such as tetramethoxytitanium, tetraethoxytitanium, tetrabutoxytitanium, dichlorodimethoxytitanium, tetraisopropoxytitanium, titanium acetate, titanium acetylacetonate and the like; phosphorus compounds, such as trimethylphosphine, triethylphosphine, tributylphosphine, triphenylphosphine, tributylmethylphosphonium halides, trioctylbutylphosphonium halides, triphenylmethylphosphonium halides and the like; zirconium compounds, such as zirconium halides, zirconocenes, zirconium acetylacetonate, zirconium alkoxides, zirconium acetate and the like; lead and lead-containing compounds, e.g., lead oxides, such as PbO, $PbO_2$, $Pb_3O_4$ and the like; lead sulfides, such as PbS, $Pb_2S_3$, $PbS_2$ and the like; lead hydroxides, such as $Pb(OH)_2$, $Pb_3O_2(OH)_2$, $Pb_2[PbO_2(OH)_2]$, $Pb_2O(OH)_2$ and the like; plumbites, such as $Na_2PbO_2$, $K_2PbO_2$, $NaHPbO_2$, $KHPbO_2$ and the like; plumbates, such as $Na_2PbO_3$, $Na_2H_2PbO_4$, $K_2PbO_3$, $K_2[Pb(OH)_6]$, $K_4PbO_4$, $Ca_2PbO_4$, $CaPbO_3$ and the like; lead carbonates and basic salts thereof, such as $PbCO_3$, $PbCO_3.Pb(OH)_2$ and the like; alkoxylead compounds and aryloxylead compounds, such as $Pb(OCH_3)_2$, $(CH_3O)Pb(OPh)$, $Pb(OPh)_2$ and the like; lead salts of organic acids, and carbonates and basic salts thereof, such as $Pb(OCOCH_3)_2$, $Pb(OCOCH_3)_4$, $Pb(OCOCH_3)_2.PbO.3H_2O$, and the like; organolead compounds, such as $Bu_4Pb$, $Ph_4Pb$, $Bu_3PbC$, $Ph_3PbBr$, $Ph_3Pb$ (or $Ph_6Pb_2$), $Bu_3PbOH$, $Ph_2PbO$ and the like wherein Bu represents a butyl group and Ph represents a phenyl group; lead alloys, such as Pb—Na, Pb—Ca, Pb—Ba, Pb—Sn, Pb—Sb and the like; lead minerals, such as galena, zinc blends and the like; hydrates of these lead compounds; ion-exchangers, such as anion-exchange resins having tertiary amino groups, amide groups, or at least one type of ion-exchange group selected from the group consisting of sulfonate, carboxylate and phosphate groups; strongly basic solid anion-exchangers having quaternary ammonium groups as ion-exchange groups and the like; solid inorganic compounds, such as silica, silica-alumina, silica-magnesia, aluminosilicate, gallium silicate, various types of zeolites, various types of metal-exchanged zeolites, ammonium-exchanged zeolites; and the like.

Preferred homogeneous transesterification catalysts include alcoholates and alkali hydroxides and carbonates, such as sodium methylate and sodium hydroxide. Preferred heterogeneous transesterification catalysts include anion exchange resins having tertiary amine, quaternary ammonium, sulfonic acid or carboxylic acid functional groups, solid support catalysts containing alkaline earth metal halides, such as those described in U.S. Pat. No. 5,498,743, which is incorporated herein by reference, or inorganic solid support catalysts alone, such as alumina, pseudoboehmite, MgO and $MgO/Al_2O_3$ hydrotalcites, or containing ions, metals, compounds or complexes of at least one element of Groups 1, 2, 4–10, 12 and 13–17 (IUPAC classification, previously Groups 1A, 2A, 4B–8B, 2B and 3A–7A) of the Periodic Table.

The specific catalyst is chosen to optimize the economics of the overall process and will depend upon the particular cyclic carbonate and aliphatic monohydric alcohol reacted, the type and amount of impurities contained in the cyclic carbonate and the transesterification reaction conditions. For example, it is contemplated that sodium hydroxide and quaternary ammonium anion exchange resins, containing some carbonate or bicarbonate anions, are particularly effective as a transesterification catalyst for the synthesis of dimethyl carbonate and ethylene glycol in accordance with the present invention. The weight ratio of homogeneous catalyst to cyclic carbonate is typically about 0.0005:1 to 0.05:1, preferably about 0.002:1 to 0.01:1. In the case of a heterogeneous catalyst, the weight hourly space velocity (WHSV) will typically be from about 0.1 to about 30, preferably about 0.5 to about 15.

The transesterification reaction is preferably carried out in a continuous mode utilizing various reactor configurations, such as stirred-tank, tubular, fixed or packed-bed reactors, in a single or multiple-reactor configuration, a boiling pot surmounted by a trayed or packed column, or a reactive distillation column, at from about 50° C. up to about 250° C., preferably between about 75° C. up to about 140° C., and at pressures ranging from about atmospheric pressure up to about 14000 Kpa (2000 psi), preferably from about 140 Kpa (20 psi) up to about 2000 Kpa (300 psi). In the preferred mode of operation, the type of reactor, temperature and pressure are optimized to insure a relatively high conversion and selectivity to the desired dialkyl carbonate and diol and to optimize the economics of the overall integrated process. Generally, a reactive distillation column will tend to give higher conversions of ethylene carbonate and methanol, while a packed-bed reactor offers flexibility in handling various heterogeneous catalysts.

In the case where the cyclic carbonate is ethylene carbonate, the transesterification reactor can be advantageously integrated with an ethylene oxide/ethylene glycol plant, where the ethylene carbonate is made by reacting ethylene oxide with carbon dioxide. At least some of the carbon dioxide may be obtained from the $CO_2$-rich waste gas stream from the ethylene oxidation process. Also, the product ethylene glycol may be sent to the glycol evaporation/distillation section of the ethylene oxide/ethylene glycol plant for final purification.

The effluent from the transesterification reaction will contain a dialkyl carbonate, diol, hydroxy alkyl carbonate, unreacted cyclic carbonate and unreacted aliphatic monohydric alcohol.

The transesterification reaction effluent is first fed to one or more separating apparatuses to separate the dialkyl carbonate product and unreacted aliphatic monohydric alcohol. Examples of such separating apparatuses include a distillation type separating apparatus, an extractive distillation type separating apparatus, a liquid-liquid extraction type separating apparatus, a crystallization type separating apparatus, an absorption type separating apparatus and a membrane type separating apparatus. A combination of a plurality of different or identical separating apparatuses may be used. Among these separating apparatuses, a distillation type separating apparatus is especially preferred. Preferably, substantially all of the unreacted aliphatic monohydric alcohol is removed from the reactor effluent as a result of the separation.

According to the present invention, it has now been found that overall yields and product purity for the dialkyl carbonate and diol can be improved if, after removing the alcohol and dialkyl carbonate, the hydroxy alkyl carbonate content in this effluent stream is diminished prior to the separation and purification steps needed to recover the diol. Preferably, the products of hydroxy alkyl carbonate decomposition are recovered and recycled to the transesterification reaction in order to maximize the product yields and improve overall process efficiency and product purity.

In one embodiment, the hydroxy alkyl carbonate in the transesterification reactor effluent stream is diminished, reduced or eliminated by converting at least a portion of the hydroxy alkyl carbonate in a conversion reaction zone under conversion conditions back to the cyclic carbonate and the aliphatic monohydric alcohol. Preferably, substantially all of the hydroxy alkyl carbonate in the effluent stream is converted back to the cyclic carbonate and the aliphatic monohydric alcohol. More preferably, substantially all of the hydroxy alkyl carbonate in the effluent stream is converted back to the cyclic carbonate and the aliphatic monohydric alcohol, and the cyclic carbonate and alcohol are recovered and recycled to the transesterification reactor.

After diminishing, reducing or eliminating the hydroxy alkyl carbonate from the transesterification reactor effluent stream, the remaining stream will typically be fed to a series of separating apparatus to recover the diol product. Examples of such separating apparatuses include the types discussed above with regard to separating the alcohol and dialkyl carbonate from the reactor effluent stream. In addition, the separated streams resulting from the use of the various separating apparatuses may also be subjected to further processing, such as additional reactions or incorporation into other chemical synthesis processes, as discussed more fully below.

One embodiment of the process, which utilizes a heterogeneous transesterification catalyst, is shown schematically in FIG. 1. Equipment not essential to the understanding of the invention such as heat exchangers, pumps, compressors and the like are not shown.

Referring now to FIG. 1, the transesterification reactor 1 is preferably a fixed bed reactor in which the cyclic carbonate is reacted with the aliphatic monohydric alcohol to form a dialkyl carbonate and a diol. The reactor, which contains the heterogeneous transesterification catalyst, is fed with cyclic carbonate via line 2 and with aliphatic monohydric alcohol via line 3. The molar ratio of alcohol to cyclic carbonate fed to the reactor is generally from about 2:1 to about 6:1, preferably about 3:1 to about 4:1. In the case of dimethyl carbonate and ethylene glycol, the reaction of ethylene carbonate and methanol will be maintained at a temperature of about 60 to 200° C., preferably about 70 to 150° C., and pressures about 700 Kpa (100 psi) to 2000 Kpa (300 psi). The conversion per pass of ethylene carbonate to dimethyl carbonate is about 30 to 70%, preferably about 50 to 65%. The WHSV is generally about 0.3 to 30 $hr^{-1}$.

The transesterification reactor effluent is withdrawn from reactor 1 via line 4. The transesterification reactor effluent 4 will contain dialkyl carbonate, a diol, hydroxy alkyl carbonate, unreacted cyclic carbonate, unreacted alcohol, and some by-products such as organic oxygenates and polyglycols. For example, in the case of a transesterification reaction between ethylene carbonate and methanol to provide dimethyl carbonate and ethylene glycol, major by-products can include dimethyl ether, 2-methoxyethanol and di-and tri-(ethylene glycols), with the reactor effluent typically containing about 10 to 30 wt % dimethyl carbonate, about 10 to 25 wt % ethylene glycol, about 2 to 10 wt % 2-hydroxyethyl methyl carbonate, 10 to 25 wt % unreacted ethylene carbonate, about 30 to 60 wt % unreacted methanol, about 0.005 to 0.05 wt % dimethyl ether/2-methoxyethanol and about 0.01 to 0.1 wt % di- and triethylene glycol. The composition, and by-product yields in particular, can vary widely based upon the specific catalysts and operating conditions employed. Inevitably, however, a significant amount of the hydroxy alkyl carbonate will be present in the transesterification effluent 4.

The transesterification reactor effluent is fed from line 4 into a distillation column or tower 5, where an overhead product stream enriched in the dialkyl carbonate, alcohol and organic oxygenates is removed via line 6 and a bottoms product stream enriched in the diol, cyclic carbonate, hydroxy alkyl carbonate and polyglycols is removed via line 7. In the case of dimethyl carbonate and ethylene glycol, distillation column 5 is typically operated at a pressure of between about 5 and 30 psia and a temperature range at the top of the column 5 of about 50 to 90° C. Optionally, a side-stream 8, which is depleted of the diol and cyclic carbonate, is withdrawn from column 5 and recycled to transesterification reactor 1, to reduce the load on the dialkyl carbonate product distillation column 9.

The overhead product stream is fed via line 6 to a dialkyl carbonate product distillation column 9, where the alcohol is taken overhead and recycled via lines 10 and 3 to transesterification reactor 1 and dialkyl carbonate product is removed as bottoms via line 11 and sent to storage. A purge stream 12 is also provided to prevent the accumulation of light by-product impurities. In the case of dimethyl carbonate, dialkyl carbonate product distillation column 9 is typically operated at a pressure of about 120 psia to 200 psia and a temperature range of about 120 to 190° C. Dimethyl carbonate and methanol form a low-boiling azeotrope, so that the overhead stream includes up to about 15 wt %, and typically about 5–15 wt % dimethyl carbonate. This dimethyl carbonate is generally recycled to transesterification reactor 1 along with methanol.

The bottoms product stream from distillation column 5 is fed via line 7 to a hydroxy alkyl carbonate conversion reactor 13, which is preferably a stirred tank reactor. The hydroxy alkyl carbonate is converted under conversion reaction conditions to cyclic carbonate and aliphatic monohydric alcohol. In the case of 2-hydroxyethyl methyl carbonate (HEMC), the temperature of the conversion reaction zone is usually maintained in the range from about 50° C. to about 130° C. and the pressure is maintained in the range from about 0.1 mmHg to about 200 mmHg, with a residence time of about 5–60 minutes.

The aliphatic monohydric alcohol is removed from conversion reactor 13 overhead via line 14 and recycled to transesterification reactor 1 via lines 14 and 3. Preferably, conversion reactor 13 is surmounted by a distillation column, which is operated under conditions sufficient to remove the aliphatic monohydric alcohol overhead and to retain the cyclic carbonate and diol for removal as a bottoms product stream.

The bottoms product stream from conversion reactor 13 is fed via line 15 to a diol product distillation column 16, where the diol product is removed overhead via line 17 and sent to storage or further processing (as discussed below), and a bottoms stream containing cyclic carbonate, polyglycols and other heavies is removed via line 18. In the case of ethylene glycol, the distillation column 16 is operated at a temperature in the range between about 100 to 170° C. and a pressure in the range between about 50 to 200 mm Hg. Bottoms stream 18 is recycled to transesterification reactor 1 via lines 18 and 2. A purge stream 19 is provided to prevent an accumulation of polyglycols and other heavies. Optionally, an evaporator can be employed to recover additional cyclic carbonate from purge stream 19. In the case of ethylene carbonate, the operating conditions of the optional evaporator typically include temperatures in the range of about 120 to 180° C. and a pressure in the range between about 10 to 80 mmHg.

In another embodiment, a hydrolysis reactor/separation unit 20 can be incorporated into the process to provide a highly purified diol, e.g., ethylene glycol. The feed to this hydrolysis reactor includes diol product stream 17, which typically contains small amounts of cyclic carbonate. Optionally, cyclic carbonate recovered from purge stream 19 and cyclic carbonate from recycle stream 18, that are otherwise recycled to transesterification reactor 1, can be fed to hydrolysis reactor/separation unit 20. A stoichometric amount of water is also fed to the hydrolysis reactor 20 via line 21. $CO_2$ is removed from hydrolysis reactor 20 overhead via line 22 and a bottoms product stream containing high purity diol is removed via line 23.

In yet another embodiment, which utilizes a homogeneous transesterification catalyst, reference will again be made to FIG. 1. In this embodiment transesterification reactor effluent 4 will contain homogeneous transesterification catalyst, in addition to the other components mentioned above. The catalyst will remain with bottoms product stream 7, following distillation in column 5. Bottoms product stream 7 can be fed to an evaporator to separate the catalyst therefrom and the separated catalyst can be recycled to transesterification reactor 1. Optionally, the catalyst will remain in bottoms product stream 7 until it is recycled with the cyclic carbonate in bottoms stream 18. Again, an evaporator can be employed to recover additional cyclic carbonate and homogeneous transesterification catalyst from purge stream 19. Make-up homogeneous transesterification catalyst is fed into line 24.

In another embodiment, the process equipment shown in FIG. 1 is used, except that hydroxy alkyl carbonate conversion reactor 13 is omitted, along with its overhead product stream 14. Column 5 is operated at temperatures greater than about 60° C. (preferably greater than about 75° C.), and pressures of about 3–100 psia, preferably about 6–40 psia, and at a residence time of liquid in column 5 sufficient to decompose the hydroxy alkyl carbonate such that the concentration of hydroxy alkyl carbonate in bottoms stream 7 is less than about 1 wt. %, and preferably less than about 0.10 wt. %. This stream is sent to column 16. The residence time of liquid in column 5, including the reboiler circuit, is preferably greater than about 30 seconds, more preferably between about 1 to 10 minutes.

Figure 2:
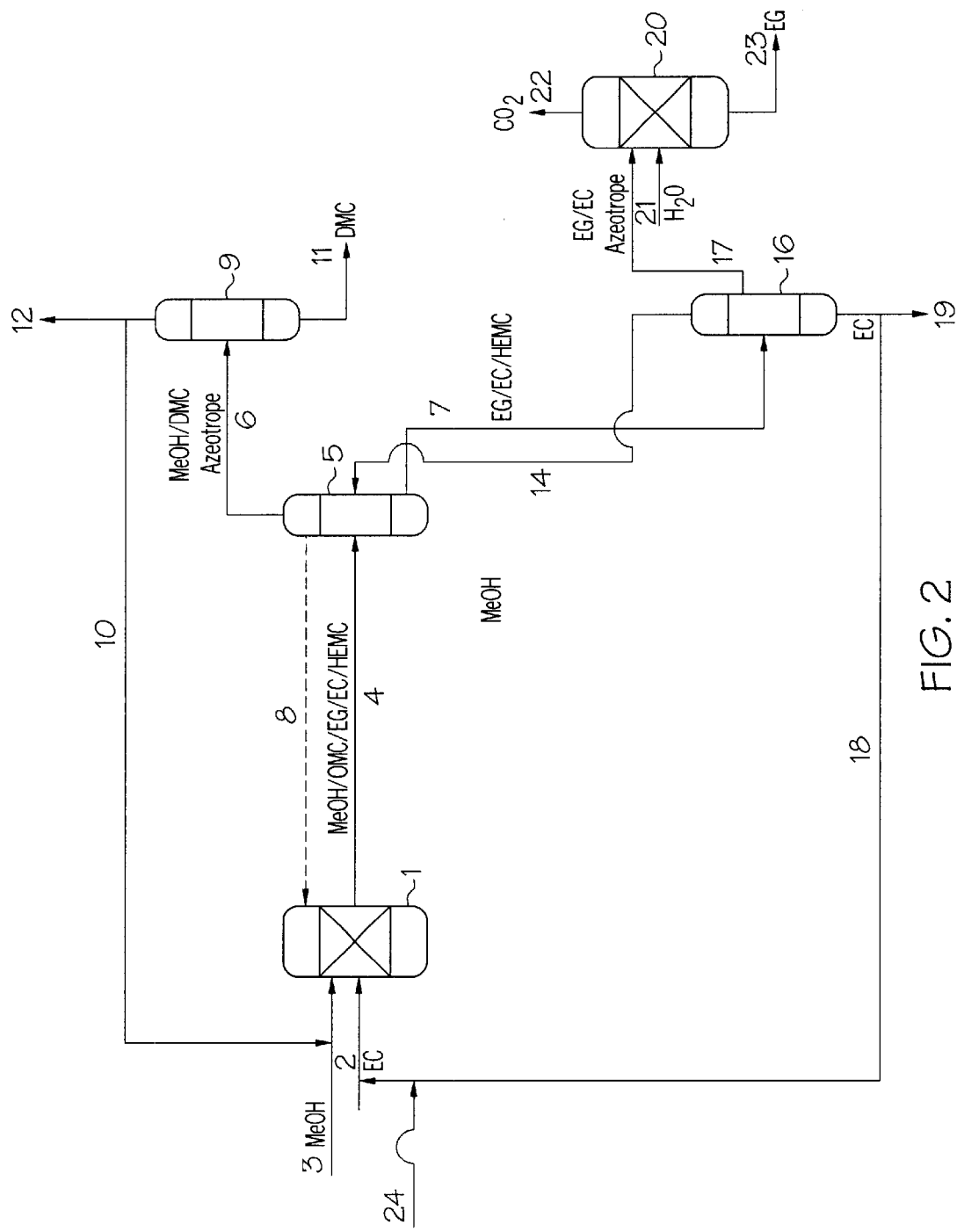
FIG. 2 is a schematic representation of another embodiment according to the present invention where the hydroxy alkyl carbonate conversion reactor 13 FIG. 1 has been removed.

As shown in FIG. 2, conversion reactor 13 is again omitted, but column 5 is operated under milder conditions, such that bottoms stream 7, contains greater than 0.1 wt. % hydroxy alkyl carbonate. This stream is sent to column 16, where glycol-rich stream 17 is separated from a cyclic carbonate-rich bottoms stream by distillation at pressure less than 15 psia. Column 16 is operated at temperatures of greater than about 50° C., preferably greater than about 75° C., and pressures less than about 15 psia, preferably less than about 2 psia, and with a liquid residence time sufficient to decompose the hydroxy alkyl carbonate such that its concentration in bottoms stream 18 is less than about 1 wt. %, and preferably less than about 0.1 wt. %. The residence time of liquid in column 16, including the reboiler circuit, is typically greater than about 30 seconds, more preferably between about 1 to 10 minutes. The decomposition of hydroxy alkyl carbonate produces aliphatic monohydric alcohol plus cyclic carbonate in column 16. To reduce contamination of the glycol-rich stream with aliphatic monohydric alcohol, the glycol-rich stream 17 is withdrawn from an intermediate point in column 16 for delivery to hydrolysis reactor/separation unit 20. $CO_2$ is removed from hydrolysis/separation reactor 20 overhead via line 22 and a bottoms product stream containing high purity diol is removed via line 23. Overhead product 14 is taken from column 16, which is enriched in the aliphatic monohydric alcohol, and sent to column 5 or alternatively to transesterification reactor 1. Cyclic carbonate-rich bottoms stream 18 is recycled to transesterification reactor via lines 18 and 2. A purge stream 19 is provided to prevent an accumulation of polyglycols and other heavies.

Figure 3:
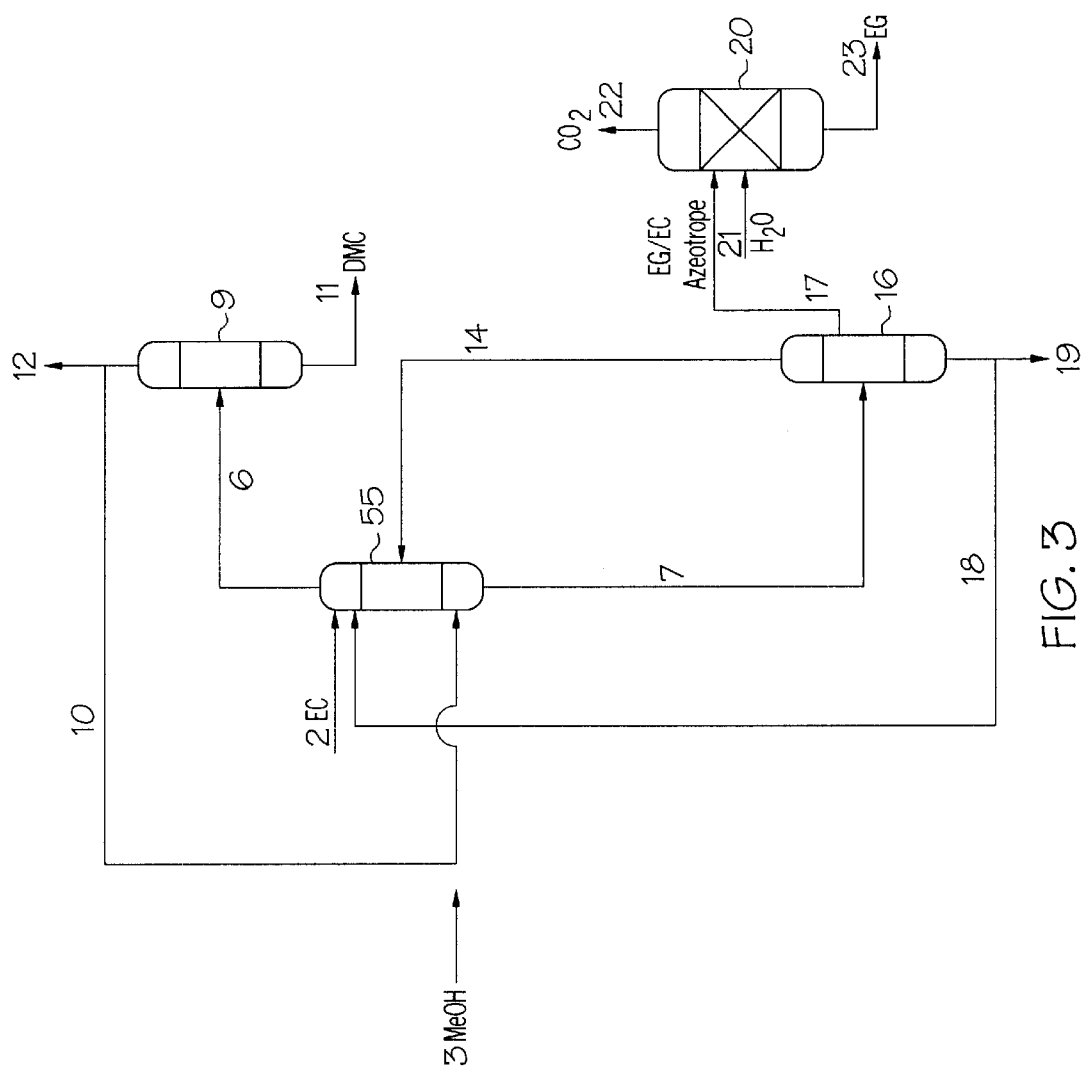
FIG. 3 is a schematic representation of the process according to the present invention which includes a reactive distillation system.

An embodiment of this process which utilizes a reactive distillation system is shown schematically in FIG. 3. In this embodiment, both reaction of a cyclic carbonate with an aliphatic monohydric alcohol and separation of a crude dialkyl carbonate stream 6 take place within reactive distillation column 55. Heterogeneous or homogeneous catalysts, or a combination of heterogeneous and homogeneous catalysts, can be used to catalyze the desired transesterification reaction. The operation of single reactive distillation column 55 maybe approximated by a distillation column or a set of columns in series, where streams, substantially of liquid, are withdrawn from at least two points from the column or columns, passed through external reaction zones, and returned to the column or columns. The type of arrangement discussed above is herein referred to as a reactive distillation system. Preferably, more than two external reaction zones are used. Each zone may be packed with solid catalysts, or simply serve as additional volume for the action of homogeneous catalyst. See U.S. Pat. No. 5,847,189 which is incorporated herein by reference. Feeds or recycle streams enriched in cyclic carbonate are preferably added near the top of reactive distillation column 55, and feeds or recycle streams enriched in aliphatic monohydric alcohol are preferably added near the bottom of column 55.

Bottoms stream 7 from reactive distillation column 55 contains at least 0.1 wt. % hydroxy alkyl carbonate. Stream 7 is sent to column 16, where a glycol-rich stream 17 is separated from a bottoms stream 18. Stream 18 is recycled to the upper region of reactive distillation column 55. Column 16 is operated at temperatures of greater than about 50° C., preferably greater than about 75° C., and pressures less than about 15 psia, preferably less than about 2 psia, and with a liquid residence time sufficient to decompose the hydroxy alkyl carbonate such that its concentration in bottoms stream 18 is less than about 1 wt. %, and preferably less than about 0.1 wt. %. The residence time of liquid in column 16, including the reboiler circuit, is typically greater than about 30 seconds, more preferably between about 1 to 10 minutes. The decomposition of hydroxy alkyl carbonate produces aliphatic monohydric alcohol plus cyclic carbonate in column 16. Substantially all of the aliphatic monohydric alcohol formed by the decomposition of the hydroxy alkyl carbonate, along with alcohol that entered column 16 as part of stream 7, is taken overhead in stream 14 and returned to reactive distillation column 55. Glycol-enriched stream 17, which preferably contains less than about 0.1 wt. % aliphatic monohydric alcohol, is withdrawn from an intermediate point of column 16.

In another embodiment involving a catalytic distillation column, the process shown in FIG. 3 is used, except stream 14 is omitted, and stream 17 is drawn from the top of column 16. The lower section of reactive distillation column 55 is operated at a pressure between about 3–100 psia, preferably between about 6–40 psia, temperatures greater than about 60° F., preferably greater than about 75° F., and a residence time for liquid sufficient to decompose the hydroxyl alkyl carbonate such that its concentration in bottoms stream 7 is less than about 1 wt. %, and preferably less than about 0.1 wt. %. The residence time of liquid in reactive distillation column 55, including the reboiler circuit below the main point of introduction of feed enriched in aliphatic monohydric alcohol is typically greater than 30 seconds, more preferably between about 1 to 10 minutes.

EXAMPLES

The following examples have been carried out to illustrate preferred embodiments of the present invention. These examples include synthesis of the intermediate 2-hydroxy ethyl methyl carbonate (HEMC) from ethylene carbonate (EC) and methanol (MeOH), isolation of a mixture of HEMC and EC, conversion of HEMC back to EC and MeOH, and a process for recovery of HEMC.

Example 1

A mixture of EC (25.6 wt %) and methanol (74.4 wt %) was allowed to react at ambient temperature (approximately 25° C.) for 1–14 days. The composition of the mixture was monitored and analyzed by GC, and the results are summarized in Table 1. Structural characterization of HEMC is shown in Example 3.

TABLE 1

Concentration Change (in wt %) of Each Component During the Reaction of EC with Methanol at 25° C.

| Reaction Time (day) | MeOH (wt %) | DMC (wt %) | EO (wt %) | HEMC (wt %) | EC (wt %) |
|---|---|---|---|---|---|
| 1 | 74.4 | 0 | 0 | 0 | 25.6 |
| 5 | 74.4 | 0 | 0 | 2.0 | 24.0 |
| 14 | 70.9 | 0 | 0.05 | 12.6 | 16.4 |

A review of Table 1 reveals that a significant amount of the intermediate HEMC was formed after 14 days at ambient temperature.

Example 2

A mixture of EC (27.1 wt %) and methanol (72.9 wt %) was allowed to react at 50° C. for 96 hours. The composition of the mixture was monitored and analyzed by GC, and the results are summarized in Table 2.

TABLE 2

Concentration Change (in wt %) of Each Component During the Reaction of EC with Methanol at 50° C.

| Reaction Time (hrs) | MeOH (wt %) | DMC (wt %) | EG (wt %) | HEMC (wt %) | EC (wt %) |
|---|---|---|---|---|---|
| 0 | 72.9 | 0 | 0 | 0 | 27.1 |
| 24 | 70.6 | 0 | 0 | 8.8 | 20.6 |
| 48 | 69.5 | 0 | 0 | 12.6 | 17.9 |
| 96 | 68.8 | 0.1 | 0.1 | 15.2 | 16.0 |

A review of Table 2 reveals that a significant amount of HEMC was formed after only 24 hours at 50° C. and that almost twice as much was formed after 96 hours at 50° C., with only minor amounts of dimethyl carbonate (DMC) and ethylene glycol (EG) being formed.

Example 3

A solution mixture containing methanol (61.5 wt %), HEMC (19.1 wt %), and EC (19.4 wt %), prepared according to a procedure similar to the one described in Example 2, was distilled under vacuum (0.6 mm Hg) at 25° C. for 75 minutes. The obtained two liquid fractions (volatile overhead fraction and high-boiling bottom fraction) were then analyzed by GC. The results show that the volatile fraction was pure methanol and the high boiling fraction contained only HEMC (49.6 wt %) and EC (50.4 wt %).

The structure of HEMC was analyzed and confirmed by field ionization mass spectroscopy and nuclear magnetic resonance spectroscopy using the HEMC/EC mixture. MS peaks and NMR resonance absorptions due to EC were identified using pure EC and subtracted during the analysis. The results are summarized as follows.

Hydroxyethyl Methyl Carbonate (HEMC)
Molecular weight: 120
$^{13}$C NMR resonances (in CDCI$_3$): 54.8, 60.6, 69.4, 155.7 ppm
$^1$H NMR resonances (in CDCI$_3$): 2.79 (1H, br), 3.79 (3H, s), 3.82 (2H, t), 4.25 (2H, t) ppm This example shows that an HEMC/EC mixture can be isolated under mild conditions, and that more severe conditions are required to decompose the HEMC.

Example 4

A solution mixture (123 g) containing HEMC (49.6 wt %) and EC (50.4 wt %) was prepared according to the procedure described in Example 3. The mixture was added to a distillation apparatus, and stirred at 75° C. for 30 minutes under vacuum (0.6 mm Hg). Dry ice was used to trap overhead volatile compounds. Two fractions were obtained, i.e., a volatile overhead liquid fraction (17.0 g) and a high-boiling solid fraction (104.0 g). GC analyses of the distillation fractions show the volatile fraction contained methanol (95.9 wt %), EC (3.6 wt %), and HEMC (0.5 wt %), and the solid fraction (analyzed in THF solution) was pure EC. Thus, the conversion of HEMC to EC and methanol was 99.9%.

This example shows that HEMC can be converted essentially quantitatively to EC and MeOH in the absence of a catalyst under relatively mild reaction conditions.

Example 5

A solution mixture containing methanol (58.2 wt %), HEMC (22.4 wt %), and EC (19.4 wt %) was prepared according to a procedure similar to the one described in Example 2. The mixture was added into a distillation apparatus and evacuated (0.6 mm Hg). Dry ice was used to trap overhead volatile compounds. The distillation pot was quickly heated to 120° C. (in less than 10 minutes) and then cooled down to room temperature. Two fractions were obtained, i.e., a volatile overhead liquid fraction and a high-boiling solid fraction. GC analyses of the distillation fractions show that the volatile fraction was pure methanol and the solid fraction (analyzed in THF solution) was EC containing 0.5 wt % of HEMC. Thus, the conversion of HEMC to EC and methanol was greater than 99.2%.

This example shows that HEMC can be converted essentially quantitatively to EC and MeOH in the absence of a catalyst more rapidly at a slightly higher temperature.

Example 6

Based on the experimental results illustrated in Examples 1–5, a process is provided to recover HEMC and maximize DMC/EG yields. According to the process, the transesterification product, MeOH/DMC/EG/EC/HEMC mixture, is first split via distillation into two streams: MeOH/DMC azeotrope mixture (approximately 30 wt % DMC and 70 wt % MeOH) and EG/EC/HEMC mixture (HEMC could be partially converted to EC and methanol during the distillation). The MeOH/DMC stream can be further separated in a high pressure distillation tower, where methanol is taken from the top and recycled back to the transesterification reactor, and pure DMC is withdrawn from the bottom of the tower. On the other hand, the EG/EC/HEMC stream is fed to an HEMC conversion reactor, where HEMC is completely converted to EC and methanol, preferably at a temperature between 50–120° C. and under vacuum. Methanol is removed upon formation and recycled back to the transesterification reactor, and EG/EC is withdrawn from the reactor bottom.

Subsequent isolation and purification of EG from EC is achieved as follows. The EG/EC mixture is initially distilled and separated into an EG/EC azeotrope fraction (containing 95 wt % EG and 5 wt % EC) and a pure EC fraction. EC is recycled back to the transesterification reactor. The EC/EG azeotrope is converted to pure EG via selective hydrolysis/decomposition of EC in an EC conversion reactor.

What is claimed is:

1. A process for the production of a dialkyl carbonate and a diol from a cyclic carbonate and an aliphatic monohydric alcohol comprising:
   (a) reacting a cyclic carbonate with said aliphatic monohydric alcohol in the presence of a transesterification catalyst to provide a crude product stream comprising said dialkyl carbonate, said diol, hydroxy alkyl carbonate, unreacted cyclic carbonate and unreacted aliphatic monohydric alcohol;
   (b) separating said dialkyl carbonate and said unreacted aliphatic monohydric alcohol from said crude product stream, thereby forming a crude dialkyl carbonate product stream and a hydroxy alkyl carbonate-rich stream;
   (c) treating said hydroxy alkyl carbonate-rich stream such that said hydroxy alkyl carbonate concentration therein is diminished, reduced or eliminated, thereby forming a hydroxyl alkyl carbonate-depleted stream; and
   (d) recovering said dialkyl carbonate from said crude dialkyl carbonate product stream and said diol from said hydroxyl alkyl carbonate-depleted stream.

2. The process of claim 1, wherein said cyclic carbonate is of the formula:

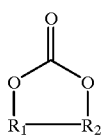

(II)

wherein $R_1$ and $R_2$ independently of one another denote a group represented by the formula —$(CH_2)_m$—, wherein m is an integer from about 1 to about 3, which is unsubstituted or substituted with at least one substituent selected from a $C_1$–$C_{10}$ alkyl group and a $C_6$–$C_{10}$ aryl group, wherein $R_1$ and $R_2$ can share the same substituent.

3. The process of claim 1, wherein said aliphatic monohydric alcohol is of the formula:

$R_3$—OH wherein $R_3$ is an aliphatic $C_1$–$C_{12}$ hydrocarbon group which is unsubstituted or substituted with at least one substituent selected from a $C_1$–$C_{10}$ alkyl group or a $C_6$–$C_{10}$ aryl group.

4. The process of claim 1, wherein said cyclic carbonate is ethylene carbonate, said aliphatic monohydric alcohol is methanol, said dialkyl carbonate is dimethyl carbonate, said diol is ethylene glycol and said hydroxy alkyl carbonate is 2-hydroxyethyl methyl carbonate.

5. The process of claim 1, wherein treating step (c) comprises converting at least a portion of said hydroxy alkyl carbonate into cyclic carbonate and/or aliphatic monohydric alcohol.

6. The process of claim 5, wherein substantially all of said hydroxy alkyl carbonate is converted to cyclic carbonate and/or aliphatic monohydric alcohol.

7. The process of claim 5, further comprising, downstream of step (c):
   (i) separating said cyclic carbonate and/or aliphatic monohydric alcohol from said hydroxyl alkyl carbonate-depleted stream; and
   (ii) recycling said cyclic carbonate and/or aliphatic monohydric alcohol to transesterification step (a).

8. The process of claim 1, wherein substantially all of said unreacted aliphatic monohydric alcohol is removed from said crude product stream, as a result of separating said crude dialkyl carbonate product stream in step (b).

9. The process of claim 1, further comprising, downstream of step (b):
   (i) separating said unreacted aliphatic monohydric alcohol from said crude dialkyl carbonate product stream; and
   (ii) recycling said unreacted aliphatic monohydric alcohol to said transesterification step (a).

10. A process for the production of a dialkyl carbonate and a diol from a cyclic carbonate and an aliphatic monohydric alcohol comprising:
    (a) reacting a cyclic carbonate with said aliphatic monohydric alcohol in the presence of a transesterification catalyst to provide a crude product stream comprising said dialkyl carbonate, said diol, hydroxy alkyl carbonate, unreacted cyclic carbonate and unreacted aliphatic monohydric alcohol;
    (b) treating said crude product stream under reaction conditions sufficient to at least partially decompose said hydroxy alkyl carbonate, thereby forming a crude dialkyl carbonate product stream; and
    (c) recovering said dialkyl carbonate and said diol from said crude dialkyl carbonate product stream.

11. The process of claim 10, wherein said cyclic carbonate is of the formula:

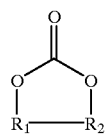

(II)

wherein $R_1$ and $R_2$ independently of one another denote a group represented by the formula —$(CH_2)_m$—, wherein m is an integer from about 1 to about 3, which is unsubstituted or substituted with at least one substituent selected from a $C_1$–$C_{10}$ alkyl group and a $C_6$–$C_{10}$ aryl group, wherein $R_1$ and $R_2$ can share the same substituent.

12. The process of claim 10, wherein said aliphatic monohydric alcohol is of the formula:

wherein $R_3$ is an aliphatic $C_1$–$C_{12}$ hydrocarbon group which is unsubstituted or substituted with at least one substituent selected from a $C_1$–$C_{10}$ alkyl group and a $C_6$–$C_{10}$ aryl group.

13. The process of claim 10, wherein said cyclic carbonate is ethylene carbonate, said aliphatic monohydric alcohol is methanol, said dialkyl carbonate is dimethyl carbonate, said diol is ethylene glycol and said hydroxy alkyl carbonate is 2-hydroxyethyl methyl carbonate.

14. The process of claim 10, wherein step (b) is conducted under the following reaction conditions: a temperature greater than about 60° C.; a pressure of between about 3 to about 100 psia; and a residence time of liquid sufficient to decompose said hydroxy alkyl carbonate.

15. The process of claim 14, wherein said hydroxy alkyl carbonate concentration in said crude dialkyl carbonate product stream is less than about 1 wt. %.

16. The process of claim 15, wherein said hydroxy alkyl carbonate concentration in said crude dialkyl carbonate product stream is less than about 0.1 wt. %.

17. A process for the production of a dialkyl carbonate and a diol from a cyclic carbonate and an aliphatic monohydric alcohol comprising:

(a) reacting a cyclic carbonate with said aliphatic monohydric alcohol in the presence of a transesterification catalyst to provide a crude product stream comprising said dialkyl carbonate, said diol, hydroxy alkyl carbonate, unreacted cyclic carbonate and unreacted aliphatic monohydric alcohol;

(b) separating said dialkyl carbonate and said unreacted aliphatic monohydric alcohol from said crude product stream, thereby forming a crude dialkyl carbonate product stream and a hydroxy alkyl carbonate-rich stream;

(c) treating said hydroxyl alkyl carbonate-rich stream under reaction conditions sufficient to at least partially decompose said hydroxy alkyl carbonate, thereby forming a diol-rich stream, a cyclic carbonate rich-stream and a aliphatic monohydric alcohol-rich stream; and (d) recovering said dialkyl carbonate from said crude dialkyl carbonate product stream and said diol from said diol-rich stream.

18. The process of claim 17, wherein said cyclic carbonate is of the formula:

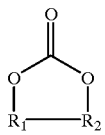

(II)

wherein $R_1$ and $R_2$ independently of one another denote a group represented by the formula —$(CH_2)_m$—, wherein m is an integer from about 1 to about 3, which is unsubstituted or substituted with at least one substituent selected from a $C_1$–$C_{10}$ alkyl group and a $C_6$–$C_{10}$ aryl group, wherein $R_1$ and $R_2$ can share the same substituent.

19. The process of claim 17, wherein said aliphatic monohydric alcohol is of the formula:

wherein $R_3$ is an aliphatic $C_1$–$C_{12}$ hydrocarbon group which is unsubstituted or substituted with at least one substituent selected from a $C_1$–$C_{10}$ alkyl group and a $C_6$–$C_{10}$ aryl group.

20. The process of claim 17, wherein said cyclic carbonate is ethylene carbonate, said aliphatic monohydric alcohol is methanol, said dialkyl carbonate is dimethyl carbonate, said diol is ethylene glycol and said hydroxy alkyl carbonate is 2-hydroxyethyl methyl carbonate.

21. The process of claim 17, wherein step (c) is conducted under the following reaction conditions: a temperature greater than about 50° C.; a pressure less than about 15 psia; and a residence time of liquid sufficient to decompose said hydroxy alkyl carbonate.

22. The process of claim 21, wherein said hydroxy alkyl carbonate concentration in said cyclic carbonate-rich stream is less than about 1 wt. %.

23. The process of claim 21, wherein said hydroxy alkyl carbonate concentration in said cyclic carbonate-rich stream is less than about 0.1 wt. %.

24. The process of claim 17, wherein step (c) occurs in a distillation reactor, wherein said diol-rich stream is taken as a side stream from said reactor, said cyclic carbonate rich-stream is taken as a bottoms stream, and said aliphatic monohydric alcohol-rich stream is taken overhead.

25. The process of claim 24, wherein said diol-rich stream is further treated to produce a high purity diol stream.

26. The process of claim 24, wherein said cyclic carbonate rich-stream is recycled to either step (a) or step (b).

27. The process of claim 24, wherein said aliphatic monohydric alcohol-rich stream is recycled to step (a).

28. A process for the production of a dialkyl carbonate and a diol from a cyclic carbonate and an aliphatic monohydric alcohol comprising:

(a) in a reactive distillation vessel, reacting said cyclic carbonate with said aliphatic monohydric alcohol in the presence of a transesterification catalyst to provide a crude dialkylcarbonate product stream comprising said dialkyl carbonate and unreacted aliphatic monohydric alcohol, and a hydroxyl alkyl carbonate-rich stream;

(b) treating said hydroxyl alkyl carbonate-rich stream under reaction conditions sufficient to at least partially decompose said hydroxy alkyl carbonate, thereby forming a diol-rich stream, a cyclic carbonate rich-stream and a aliphatic monohydric alcohol-rich stream; and (c) recovering said dialkyl carbonate from said crude dialkyl carbonate product stream and said diol from said diol-rich stream.

29. The process of claim 28, wherein said cyclic carbonate is of the formula:

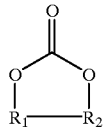

(II)

wherein $R_1$ and $R_2$ independently of one another denote a group represented by the formula —$(CH_2)_m$—, wherein m is an integer from about 1 to about 3, which is unsubstituted or substituted with at least one substituent selected from a $C_1$–$C_{10}$ alkyl group and a $C_6$–$C_{10}$ aryl group, wherein $R_1$ and $R_2$ can share the same substituent.

30. The process of claim 28, wherein said aliphatic monohydric alcohol is of the formula:

$$R_3\text{—OH}$$

wherein $R_3$ is an aliphatic $C_1$–$C_{12}$ hydrocarbon group which is unsubstituted or substituted with at least one substituent selected from a $C_1$–$C_{10}$ alkyl group and a $C_6$–$C_{10}$ aryl group.

31. The process of claim 28, wherein said cyclic carbonate is ethylene carbonate, said aliphatic monohydric alcohol is methanol, said dialkyl carbonate is dimethyl carbonate, said diol is ethylene glycol and said hydroxy alkyl carbonate is 2-hydroxyethyl methyl carbonate.

32. The process of claim 28, wherein step (b) is conducted under the following reaction conditions: a temperature greater than about 50° C.; a pressure less than about 15 psia; and a residence time of liquid sufficient to decompose said hydroxy alkyl carbonate.

33. The process of claim 32, wherein said hydroxy alkyl carbonate concentration in said crude dialkyl carbonate product stream is less than about 1 wt. %.

34. The process of claim 33, wherein said hydroxy alkyl carbonate concentration in said crude dialkyl carbonate product stream is less than about 0.1 wt. %.

35. The process of claim 28, wherein step (b) occurs in a separate distillation reactor, wherein said diol-rich stream is taken as a side stream from said reactor, said cyclic carbonate rich-stream is taken as a bottoms stream, and said aliphatic monohydric alcohol-rich stream is taken overhead.

36. The process of claim 35, wherein said diol-rich stream is further treated to produce a high purity diol stream.

37. The process of claim 35, wherein said cyclic carbonate rich-stream and said aliphatic monohydric alcohol-rich stream are recycled to step (a).

38. A process for the production of a dialkyl carbonate and a diol from a cyclic carbonate and an aliphatic monohydric alcohol comprising:
   (a) in a reactive distillation vessel, (i) reacting said cyclic carbonate with said aliphatic monohydric alcohol in the presence of a transesterification catalyst to provide a crude dialkylcarbonate product comprising said dialkyl carbonate and unreacted aliphatic monohydric alcohol, and a hydroxyl alkyl carbonate-rich product; and (ii) treating said hydroxyl alkyl carbonate-rich product under reaction conditions sufficient to at least partially decompose said hydroxy alkyl carbonate, thereby forming a diol-rich stream, a cyclic carbonate rich-stream and a aliphatic monohydric alcohol-rich stream; and
   (b) recovering said dialkyl carbonate from said crude dialkyl carbonate product stream and said diol from said diol-rich stream.

39. The process of claim 38, wherein said cyclic carbonate is of the formula:

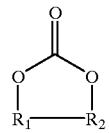

(II)

wherein $R_1$ and $R_2$ independently of one another denote a group represented by the formula —$(CH_2)_m$—, wherein m is an integer from about 1 to about 3, which is unsubstituted or substituted with at least one substituent selected from a $C_1$–$C_{10}$ alkyl group and a $C_6$–$C_{10}$ aryl group, wherein $R_1$ and $R_2$ can share the same substituent.

40. The process of claim 38, wherein said aliphatic monohydric alcohol is of the formula:

$$R_3\text{—OH}$$

wherein $R_3$ is an aliphatic $C_1$–$C_{12}$ hydrocarbon group which is unsubstituted or substituted with at least one substituent selected from a $C_1$–$C_{10}$ alkyl group and a $C_6$–$C_{10}$ aryl group.

41. The process of claim 38, wherein said cyclic carbonate is ethylene carbonate, said aliphatic monohydric alcohol is methanol, said dialkyl carbonate is dimethyl carbonate, said diol is ethylene glycol and said hydroxy alkyl carbonate is 2-hydroxyethyl methyl carbonate.

42. The process of claim 38, wherein step (a) is conducted under the following reaction conditions: a temperature greater than about 50° C.; a pressure less than about 15 psia; and a residence time of liquid sufficient to decompose said hydroxy alkyl carbonate.

43. The process of claim 42, wherein said hydroxy alkyl carbonate concentration in said crude dialkyl carbonate product stream is less than about 1 wt. %.

44. The process of claim 43, wherein said hydroxy alkyl carbonate concentration in said crude dialkyl carbonate product stream is less than about 0.1 wt. %.

* * * * *